United States Patent [19]

Blake

[11] 4,328,182

[45] May 4, 1982

[54] STERILIZATION INDICATORS CONTAINING AMINO ACID(S) AND PH INDICATOR

[75] Inventor: Graham J. Blake, Langham, England

[73] Assignee: Albert Browne Limited, England

[21] Appl. No.: 197,544

[22] Filed: Oct. 16, 1980

[30] Foreign Application Priority Data

Oct. 24, 1979 [GB] United Kingdom ............... 36833/79

[51] Int. Cl.³ ...................... G01N 31/22; G01N 33/52
[52] U.S. Cl. ...................................... 422/56; 116/206; 252/408; 435/805
[58] Field of Search .......................... 422/56; 435/805; 116/206 X

[56] References Cited

U.S. PATENT DOCUMENTS

| | | | |
|---|---|---|---|
| 3,386,807 | 6/1968 | Edenbaum | 422/56 |
| 3,409,405 | 11/1968 | Mohan | 422/56 X |
| 3,852,034 | 12/1974 | Gunther | 422/56 X |
| 3,862,824 | 1/1975 | Chapman | 422/56 |
| 3,875,014 | 4/1975 | Forgione | 435/805 |
| 3,945,798 | 3/1976 | Young | 422/56 X |
| 4,015,937 | 4/1977 | Miyamoto | 116/206 X |
| 4,179,397 | 12/1979 | Rohowetz | 23/230 R X |
| 4,240,926 | 12/1980 | McNeely | 116/206 X |
| 4,247,297 | 1/1981 | Berti | 435/805 X |

*Primary Examiner*—Sidney Marantz
*Attorney, Agent, or Firm*—Richard H. Zaitlen

[57] ABSTRACT

An indicator which is used for indicating the completion of a sterilization process in which an article to be sterilized is exposed to formaldehyde vapor either dry or mixed with steam. The indicator comprises a mixture of preferably two amino acids and a pH indicator impregnated in a paper carrier. The amino acids and pH indicator are such that the change point of the pH indicator lies within the range of the change of pH value of the amino acid mix which occurs on exposure of the amino acids to formaldehyde vapor.

9 Claims, No Drawings

STERILIZATION INDICATORS CONTAINING AMINO ACID(S) AND PH INDICATOR

The present invention relates to a means for indicating the completion of a sterilisation process in which an article to be sterilised is exposed to formaldehyde vapour. The formaldehyde vapour may be in a steam and formaldehyde vapour mix.

Sterilisation techniques based on the exposure of an article to steam and formaldehyde vapour are becoming increasingly important, particularly in hospitals, primarily because of the low toxicity and small fire risks associated with formaldehyde. It is, however, essential to test the efficiency of such a sterilisation cycle to ensure that the article has been exposed to formaldehyde vapour for sufficient time to allow a sufficient dose of the formaldehyde vapour to reach all parts of the article. The levels of formaldehyde necessary for sterilisation are quite large by normal analytical standards so that existing analytical techniques are normally too sensitive for this application. Attempts have been made to modify some of the existing analytical techniques to cope with the large concentrations of formaldehyde but these have hitherto proved unsuccessful for the following reasons.
(a) Chromotropic Acid—this test requires a concentrated sulphuric acid environment which makes its application difficult (Morath and Woods Anal. Chem. 30 1437 1958);
(b) Schiff reagent —this is unstable before exposure to formaldehyde and has a poor shelf life (Schiff Ann. 92 1866; Kasten International Reviews of Cytology 10 1960);
(c) Sulphite/pH indicator —The colours of the indicator are not permanent, for example at high pH value the magenta colour of phenolphthalein fades after exposure, and at low pH value a spontaneous change from yellow to purple can occur in the colour of m-cresol purple before exposure (Lemme Chemiker Zgt. 27 896 1903; Siggia and Maxey Ind. Eng. Chem. (Anal. Ed.) 19 1023 1947);
(d) Hantzsch/Nash reaction —the colour change from white to yellow is not very distinctive (Gindler Clin. Chem. 23(6) 1153 77M 1R; Nash Biochem J. 1953 55 416);
(e) Hydrazine/pH indicator —the reaction of this with formaldehyde is reversible (Fuchs Sci. Pharm. 16 50 1948; 17 1 1949);

The present invention seeks to provide an improved form of indicator.

Accordingly the present invention provides an indicator for indicating completion of a sterilisation process in which an article to be sterilised is exposed to formaldehyde vapour, wherein the indicator comprises a carrier and a mixture of at least one amino acid and a pH indicator on said carrier chosen such that the change point of the pH indicator lies within the range of the change of pH value of said amino acid which occurs on exposure of the amino acid to formaldehyde vapour.

The amino acids can be natural or synthetic, aliphatic or aromatic—primary or secondary—but preferably aliphatic primary.

The carrier is preferably a neutral, absorbent paper such as filter paper, which may be impregnated with the amino acid and pH indicator. Alternatively the carrier could be a portion of the article or article packaging coated with the amino acid and pH indicator mixture.

The mixture may conveniently be applied to the carrier by printing or similar method.

The present invention is based on the Sorenson reaction: (Biochem. Z. 45-101 1908 C.A. 2 1288)

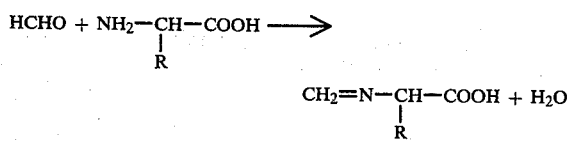

that is, formaldehyde reacts with an amino acid to reduce the pH value of the acid.

When the amino acid is added to a pH indicator of a suitable pH value the resulting change in pH value of the amino acid when exposed to formaldehyde is exhibited as a change in the colour of the pH indicator. The best condition for the reaction is an initially neutral pH, the resulting Schiff base being stable provided the pH value is not too low.

The pH indicator may first be chosen for its colour change and then the amino acid chosen to provide a pH change on exposure to formaldehyde, which pH change passes through the pH change point of the indicator. Where no single amino acid is suitable a buffer may be added to an amino acid of low pH to raise the pH value, or two or more amino acids may be mixed to provide a resulting mixture with a suitable initial pH value and pH change. Alternatively an amino acid or mixture of amino acids may be selected and then a suitable pH indicator chosen.

The mixture of one or more amino acids and pH indicator is made up in solution using neutral pH water such as distilled water. The carrier is then dipped in the solution and allowed to dry. Once dry the carrier is then provided with a coating which protects the mixture from handling and also from dilution and loss by steam when exposed to steam and formaldehyde vapour but allows contact with formaldehyde. This is effected by dipping the carrier in a suitable solution such as a silicone solution with a built in curing agent and allowing this to dry. Dow Corning 27046 is a preferred silicone solution. Where the resulting indicator is to be exposed to dry formaldehyde vapour the protective coating may be omitted.

The time taken from initial exposure of the resulting indicator to steam and formaldehyde vapour to completion of the pH indicator colour change depends upon, for example, the concentration of formaldehyde, the rate of change of the pH value of the amino acid or mixture of amino acids and the concentration of the amino acid/indicator solution. The protective coating also introduces a time delay. All these factors can be adjusted to ensure the exposure time required for pH indicator colour change is sufficient to ensure complete sterilisation.

EXAMPLE I

Bromo cresol purple was chosen as a pH indicator since it has a sharp colour change from purple to yellow as the pH drops through a value of approximately 6.0. An amino acid with an initial $pH_I$ of about 6.5 was therefore required but since such an amino acid was not conveniently available a mixture of Glycine ($pH_I$ 6.0) and Histidine ($pH_I$ 7.8) was chosen to provide a solution with an initial pH of about 6.5 which drops approximately to pH 5.0 after full exposure to formaldehyde.

($pH_I$, the isoelectric point for an amino acid, is defined as $$pH_I = \frac{pK_1 + pK_2}{2}$$

where $pK_1$ and $pK_2$ are the pK values of the two dissociatable groups in the amino acid)

6 cm³ of a 10% aqueous solution of Histidine was mixed with 6 cm³ of a 20% aqueous solution of Glycine and 3 cm³ of a 2.5% alcoholic solution of bromo cresol purple. The resulting solution was warmed and thoroughly stirred. Whatman No. 1 filter paper was dipped in the solution and dried in a hot air stream. The dried paper was then dipped in a solution of Dow Corning Silicone 27046 and dried by warming in an air stream. It was dipped and dried again to provide an adequate coating of silicone and then cured in an oven at 120° C. for 1 minute. Curing can be effected at room temperature although this naturally takes longer.

In a laboratory test of the effectiveness of the colour change, exposure to the vapour of boiling 5% formaldehyde solution caused the paper colour to change from deep purple to bright yellow after about 3 minutes. The yellow colour which indicated substantial contact with formaldehyde was stable and did not revert to purple or fade over a storage period of one month. Further tests were carried out to establish the effectiveness of the sterilisation indicator using a Drayton Castle Formaldehyde Sterilizer as follows:

The indicator was placed in a chamber of 21 cu. ft., and subjected to a total of 620 ml Formalin in 15 pulses spread over 19 minutes at a holding time of 2 hours at a temperature of 73°–75° C. Air pulsing for the removal of the formaldehyde and drying made a total cycle time of 3 hrs. 10 mins. The results obtained showed that the colour changes of the indicator followed closely the death of spore strips. Adjustments can be made to the indicator to allow a degree of safety matching the death of the spores.

EXAMPLE II

In this example the pH indicator was made up of a 2.5% alcoholic solution of Bromo cresol purple and a 1% aqueous solution of alkaline aniline blue containing 90 cm³ molar sodium hydroxide per liter. The amino acid chosen was a mixture of amino acids Glycine ($pH_I$ 6.0) and Arginine ($pH_I$ 10.8). The mixture has the advantage that relatively less Arginine is required than Histidine in Example I and the mixture is more easily dissolved in water or an alcohol-water mixture. Ethanol is in fact a preferred alcohol because of its volatility.

400 gms of Glycine and 160 gms of Arginine were dissolved in about 3 liters of deionised water. 280 cm³ of the 2.5% alcoholic solution of Bromo cresol purple and 200 cm³ of the 1% aqueous alkaline solution of aniline blue were added to the amino acid mixture. The mixture was then made up to 4.5 liters with 70 o.p. ethanol and shaken to ensure homogeneity. The pH of the resulting solution should be 8.5.

Whatman No. 1 filter paper was dipped into the solution and dried quickly in warm air. The dried paper was then coated with a protective layer of silicone as follows:

100 cm³ of Dow Corning 27046 was mixed with 100 cm³ "Genclene" (an ICI product containing mainly 1.1.1. trichlorethane) and 10 cm³ of Dow Corning Q 27047 catalyst added. The mixture was thoroughly stirred to ensure homogeneity. The dried paper was dipped into the silicone solution and passed through a slit of width 0.022 inches to provide a silicone coating of reasonably accurate thickness and dried in warm air. Once dry, the paper was once again dipped in the silicone solution, passed through the slit and dried. The paper was then tested as follows:

(a) A 1 cm² piece of the paper was suspended in the vapour of boiling 1% aqueous formaldehyde solution (prepared by diluting commercial formalin 40 times) and the time taken for the Royal Blue paper to change substantially to Apple Green, measured. With the above formulation about 3 minutes is required.

(b) A more realistic test was performed on a British Steriliser Co. 21 cu.ft. formaldehyde sterilizer by introducing 35 cm³ of 40% aqueous formalin into the evacuated sterilizer and raising the total pressure with steam at 73° C. to 277 torr. The pressure was then reduced to 74 torr by pumping, the time for the latter pulse being about 5 minutes. After 6 such pulses, the Royal Blue colour of the indicator paper began to change to Apple Green, the change being complete at about pulse 8.

Increasing the proportion of Arginine relative to Glycine in the indicator delays the colour change while increasing the proportion of Glycine accelerates the colour change. Thus the indicator may be modified to indicate different desired sterilising times. The timing of the colour change may also be achieved by varying the thickness and number of the applied silicone coatings.

I claim:

1. An indicator for indicating completion of a sterilisation process in which an article to be sterilised is exposed to formaldehyde vapour, the indicator consisting essentially of a carrier, and a mixture of at least one amino acid and a pH indicator deposited on said carrier and chosen such that the change point of the pH indicator lies within the range of the change of pH value of said amino acid which occurs on exposure of the amino acid to formaldehyde vapour.

2. An indicator was claimed in claim 1 further comprising a buffer agent added to said at least one amino acid for adjusting the pH value of said amino acid to a desired pH value.

3. An indicator as claimed in claim 1 or 2 wherein a protective coating is provided on said mixture, for partially restricting the passage therethrough of steam when the indicator is exposed to a formaldehyde and steam vapour mix.

4. An indicator as claimed in claim 3 wherein said coating is a silicone coating.

5. An indicator as claimed in claim 1 wherein said carrier is a substantially neutral, absorbent fabric impregnated with said mixture.

6. An indicator as claimed in claim 1 wherein the or each amino acid is an aliphatic primary amino acid.

7. An indicator as claimed in claim 1 wherein said mixture is arranged to have a substantially neutral pH value prior to exposure to formaldehyde vapour.

8. An indicator as claimed in claim 1 wherein the mixture contains both Glycine and Histidine.

9. An indicator as claimed in claim 1 wherein the mixture contains both Glycine and Arginine.

* * * * *